United States Patent [19]

Kinrade

[11] Patent Number: 5,015,590
[45] Date of Patent: May 14, 1991

[54] METHOD OF DETERMINING NITROGEN DIOXIDE CONCENTRATION IN A GAS SAMPLE WHICH CONTAINS OZONE

[75] Inventor: John D. Kinrade, Egbert, Canada
[73] Assignee: Scintrex Limited, Concord, Canada
[21] Appl. No.: 207,114
[22] Filed: Jun. 14, 1988
[51] Int. Cl.$^5$ ............................................. G01N 21/00
[52] U.S. Cl. .................................... 436/117; 436/116; 436/118; 436/135; 436/172
[58] Field of Search ............... 436/117, 118, 135, 172, 436/116

[56] References Cited

U.S. PATENT DOCUMENTS 3,677,708 7/1972 Harman et al. ................ 23/232 R
4,765,961 8/1988 Schiff et al. ......................... 422/52

OTHER PUBLICATIONS

Schiff et al., Water, Air and Soil Pollution 30, (1986), pp. 105–114.

Primary Examiner—David L. Lacey
Assistant Examiner—David Redding
Attorney, Agent, or Firm—Sim & McBurney

[57] ABSTRACT

The interference of ozone in the determination of nitrogen dioxide determinations by luminol chemiluminescence is eliminated by first passing the gas sample into contact with a selective reducing agent for ozone, particularly antimony trioxide.

5 Claims, 4 Drawing Sheets

METHOD OF DETERMINING NITROGEN DIOXIDE CONCENTRATION IN A GAS SAMPLE WHICH CONTAINS OZONE

FIELD OF INVENTION

The present invention relates to analyzing gas streams, particularly the nitrogen dioxide content of gas streams.

BACKGROUND TO THE INVENTION ent of the concentrations of minor components of air is routinely carried out. One of those components is nitrogen dioxide and its measurement is effected using luminol chemiluminescence. This procedure and equipment therefor is described by Schiff et al in U.S. Pat. No. 4,765,961 and reference may be had thereto for details thereof.

The measurement is rapid and sensitive. For example, the Luminox instrument, LMA-3, used in such measurements weighs only 7 kg and yet has a detection limit of 5 ppt (i.e. parts per trillion) with a time response of the order of 1 second.

Unfortunately, ozone interferes with the accuracy of the measurement for nitrogen dioxide. In some environments, this interference is not particularly significant, for example, in urban environments where there are relatively high concentrations of NO and hence $NO_2$ from automobile traffic. However, in clean tropospheric background air, ozone interference becomes major.

SUMMARY OF INVENTION

In accordance with the present invention, this prior art problem of determination of the concentration of $NO_2$ in a gas sample containing both $NO_2$ and ozone is overcome by selectively removing the ozone from the gas sample prior to measuring the $NO_2$ concentration. By making a determination on the gas sample without selective removal of ozone, it is possible also to determine the concentration of ozone in the sample.

Accordingly, the present invention provides, in one aspect, an improvement in a method of determining the concentration of nitrogen dioxide in a gas sample containing nitrogen dioxide and ozone. The improvement comprises selectively removing ozone from the gas sample prior to the determination by contacting the gas sample with a reducing agent having a redox potential below that of ozone and above or near that of nitrogen dioxide.

Further, the present invention provides, in another aspect, a method of determining the concentrations of nitrogen dioxide and ozone in a gas sample by luminol chemiluminescence by a multi-step operation. A first determination of the nitrogen dioxide in the gas sample is made by luminol chemiluminescence. The gas sample then is passed into contact with a selective reducing agent for ozone in preference to nitrogen dioxide. A second determination of the nitrogen dioxide concentration in the gas sample then is made by luminol chemiluminescence as the true determination of the nitrogen dioxide concentration in the gas sample. The second determination is subtracted from the first determination to provide a third determination corresponding to the ozone concentration of the gas sample.

GENERAL DESCRIPTION OF INVENTION

In the present invention, selective removal of ozone from the gas sample may be effected by passing a stream of the gas in contact with a reducing agent having a redox potential below that of ozone but above or near that of nitrogen dioxide. When the selected removal has been effected, the concentration of nitrogen dioxide made is the true measurement of the concentration of that gas in the original gas sample.

A particularly useful material for effecting ozone removal is antimony oxide ($Sb_2O_3$), which during reduction of the ozone is oxidized to its pentavalent state. Other materials which are useful in the present invention are other multivalent metal oxides including arsenic trioxide ($As_2O_3$), thallous oxide ($Tl_2O$), vanadous oxide ($V_2O_4$), manganous oxide ($Mn_3O_4$) and cuprous oxide ($Cu_2O$).

It is preferred to use oxides for reasons of ease of handling, good temperature stability and low water affinity. However, other compounds, such as sulfates, chlorides and nitrates, also may be used, although they may exhibit less desirable characteristics.

The selective reducing agent generally is used in particulate form to provide a large surface area of contact and may be provided on a suitable support in a chamber through which the gas stream passes.

Determination of the concentration of the nitrogen dioxide in the gas sample may be effected in any convenient manner, preferably the luminol chemiluminescence procedure, described in the Schiff et al article referred to above.

The nitrogen dioxide concentration also may be determined prior to contact of the gas sample with the ozone reducing agent, which determination represents a determination both of nitrogen dioxide and interference in the determination by the ozone.

Subtraction of the determination after ozone removal from that obtained prior to ozone removal thereby provides a measure of the concentration of ozone in the original gas sample.

EXAMPLES

Example 1

An ozone trap was prepared comprising 54 cm$^3$ of cotton wool as a support dusted with powdered $Sb_2O_3$. The trap was contained in a 47 mm filter holder. A 30 micron Teflon filter was used to ensure that the oxide dust did not migrate to an LMA-3 $NO_2$ detector provided in line with the trap.

Tests were run with the trap in the line and with the trap out of the line for various concentrations of $NO_2$ in a gas stream and containing 40 ppb of $O_3$. The results obtained were plotted graphically and are reproduced as FIGS. 1 to 4.

Figure 1:
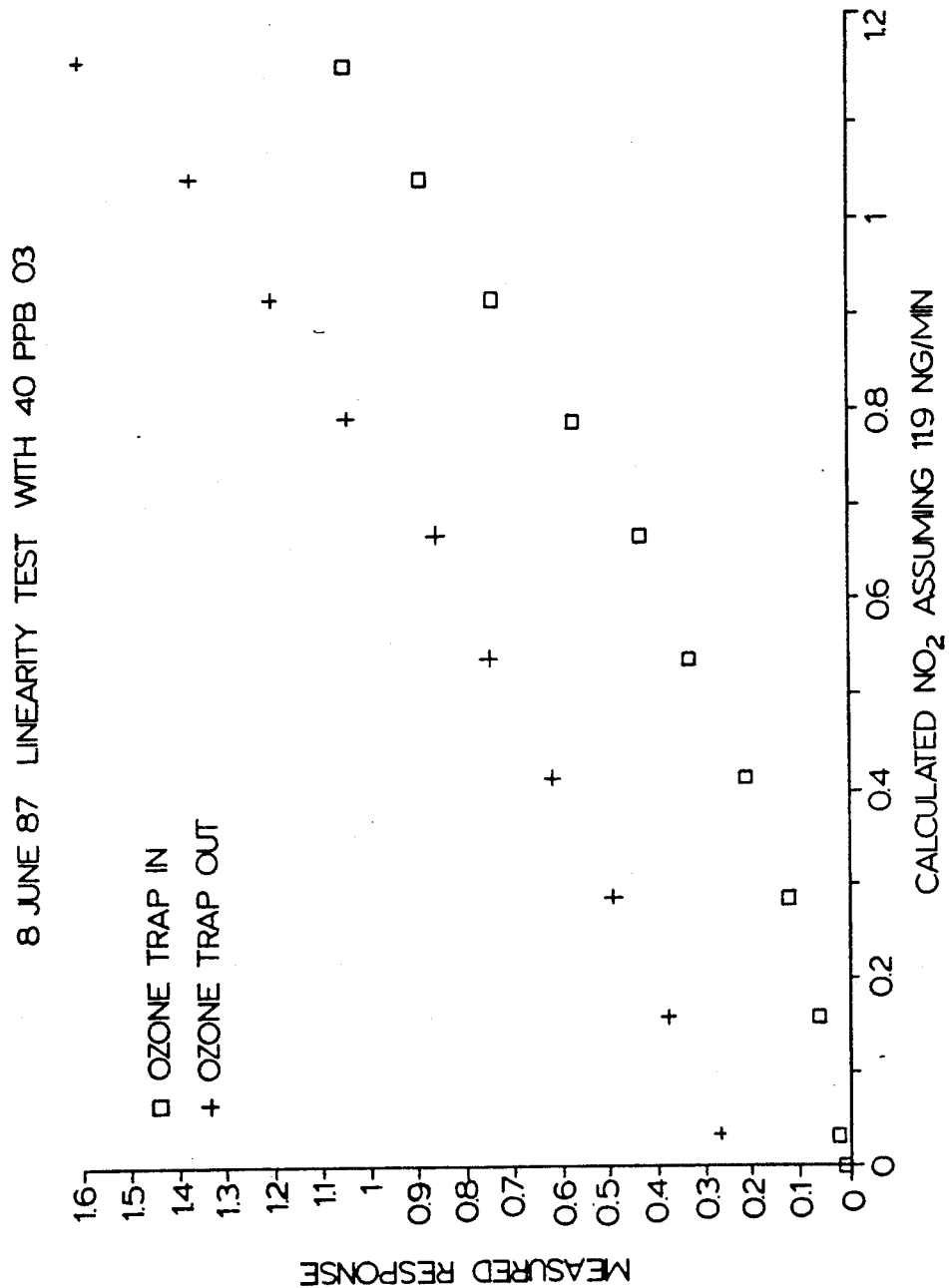
FIG. 1 to 3 are graphical representation of data presented in Example 1 below.

As may be seen from FIG. 1, the increase in the signal from the LMA-3 instrument normally attributable to ozone was undetectable with the ozone trap in the line. The relationship of the LMA-3 signal to $NO_2$ concentration is linear, although the $NO_2$ signal was approximately 5% below that normally expected for linearity tests for $NO_2$ without ozone.

Figure 2:
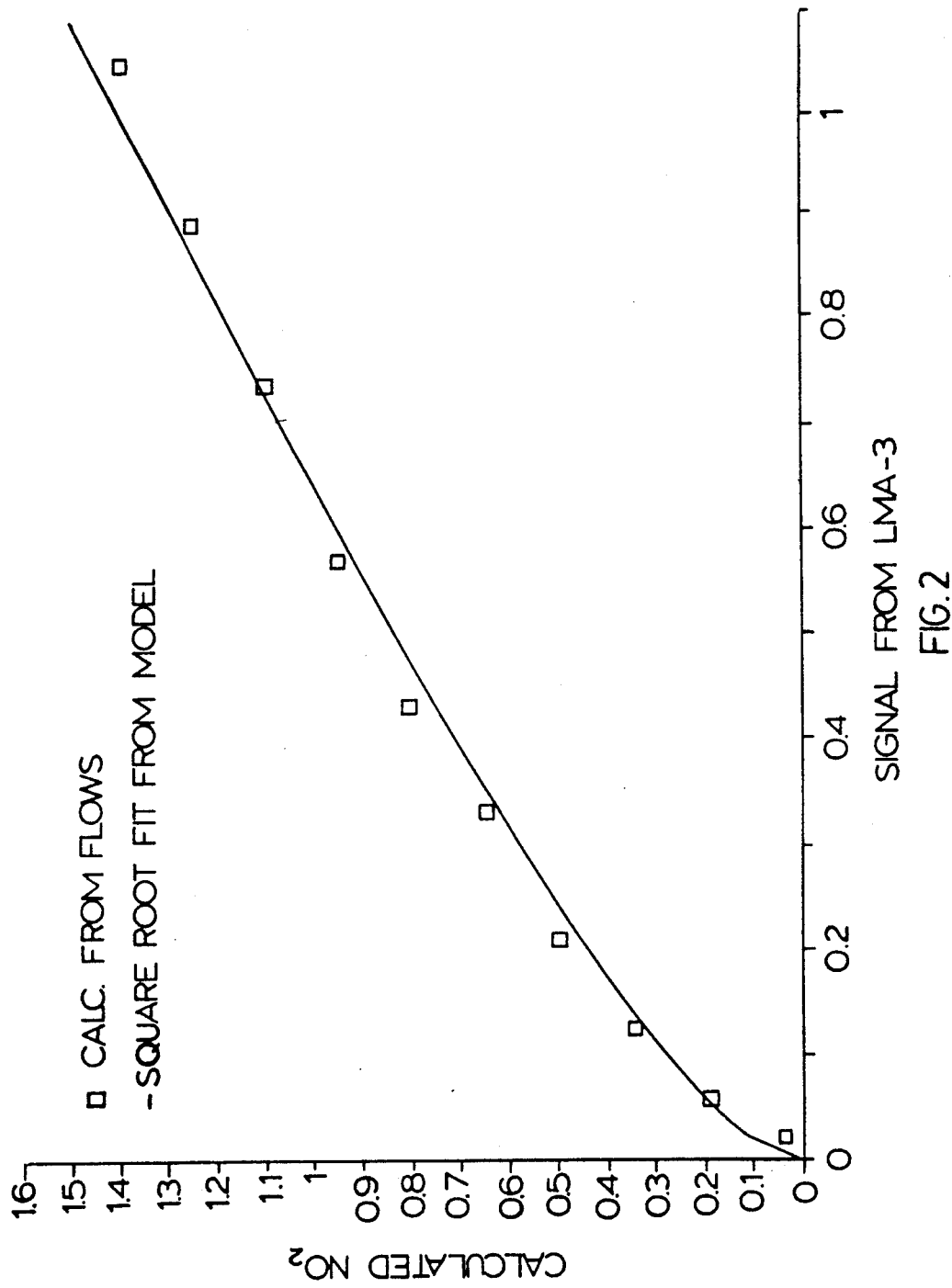
Figure 3:
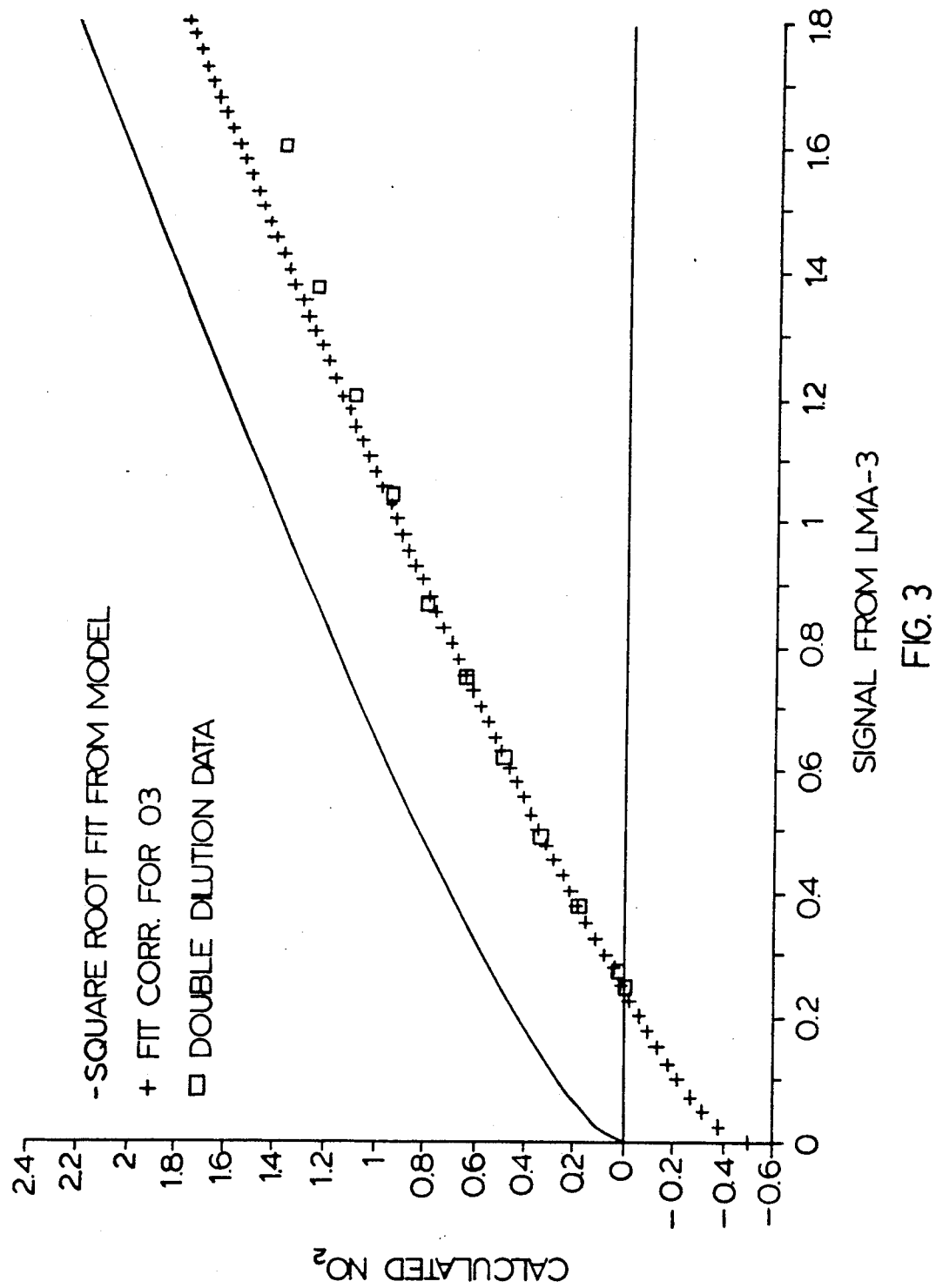

The measurements shown in FIG. 1 have been replotted with reversed axis in FIGS. 2 and 3. For reference purposes, a curve representing a computer model for the LMA-3 non-linearity is shown in each Figure. In FIG. 3, the model curve has displaced by subtracting a constant value to generate the curve denoted by the "+" symbols, demonstrating that the linearity behavior for $NO_2$ using the trap is preserved within about 5%. Note that $O_3$ (at least for sub-ppb concentrations of $NO_2$) has the same effect as $NO_2$ on the LMA-3 response.

Example 2

Ozone diluted with air or oxygen was passed through traps containing various volumes of cotton wool, shaken to saturation with antimony oxide powder, and the resulting ozone was determined by an ozone monitor.

A first test was carried out with an ozone/oxygen mixture and only 1.5 cm$^3$ of destruction material was used in a simple polypropylene drying tube trap. The flow rate of the oxygen/ozone mixture flowing through the trap was 40 cm$^3$/min and its mixing ratio was 4.2 ppm. (In order to determine the ozone mixing ratio in the test stream, it was further diluted with air flowing at 2.0 l/min, in and then monitored by a Dasibi Ozone monitor model 1008-AH. The $O_3$ was calculated by multiplying those measurements by the ratio of the flows, 2.4/0.4). The contact time was 2.2 s. Ozone at this extremely high mixing ratio broke through the trap with a time constant of 18 minutes.

This result can be used to estimate the lifetime under nominal atmospheric concentrations of ozone and for a trap containing 54 cm$^3$ of the destruction material. For 40 ppb of ambient ozone, such a trap should last 1260 h, or roughly 50 days. This result was obtained by multiplying 18 minutes by the ratio of the ozone mixing ratios and the ratio of the trap volumes. For this calculation, it was assumed that the contact time should not play a role.

A second test was carried out on 3.0 cm$^3$ of material at a mass flow rate of 5 l/min and a measured ozone content of 180 ppm. No breakthrough of ozone was observed over a period of 3 hours. In this case, the contact time was 0.04 secs and the $NO_2$ loss through the trap was 4.5%.

Example 3

A prototype trap comprising 60 cm$^3$ of cotton wool saturated with powdered antimony trioxide followed by a 40 to 60 micron Teflon filter has been provided in line with an LMA-3 $NO_2$ detector. The detector functioned without loss in ozone scrubbing efficiency over a 9 week period during which the unit was used to detect NO2 concentrations for atmospheric air having concentrations of ozone varying from 10 to 120 ppb. The duty cycle was 12.5%.

Figure 4:
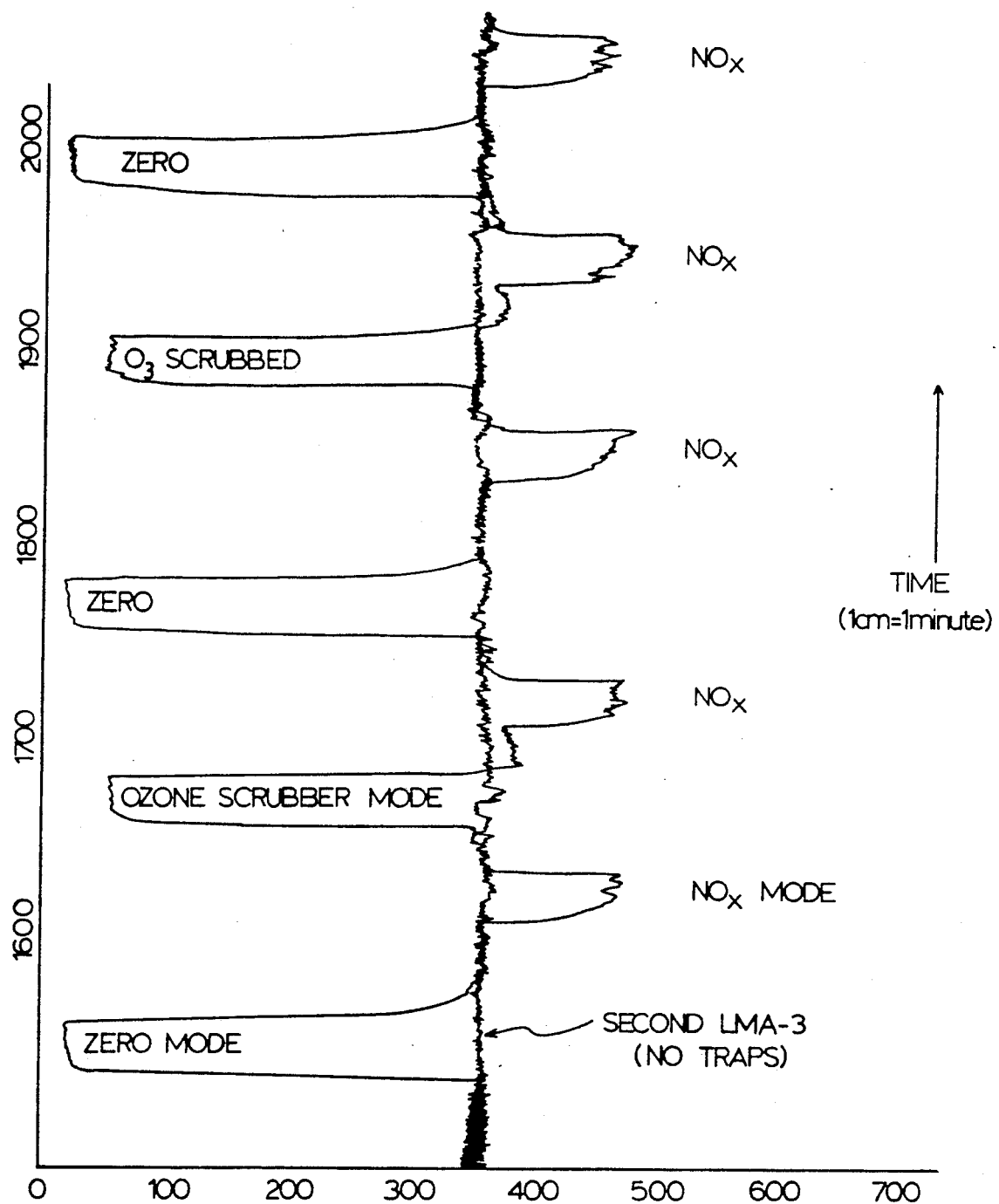
FIG. 4 is a raw chart trace of ambient air measurements, discussed in Example 3 below.

FIG. 4 shows the raw chart trace of actual ambient air measurements taken at Niwot Ridge, Colorado in July, 1987. These measurements show clearly the extent to which ozone can interfere with the LMA-3 when measuring very clean background air.

There are four different signals shown in FIG. 4, whose meanings are as follows. The zeros are the LMA-3 signals when the ambient air has been scrubbed of both ozone and $NO_2$. They have been offset by 20 ppt to avoid the possibility of negative signals to the data logger. The ozone scrubbed mode gives the signal for $NO_2$. During the data analysis, it must first be corrected by subtracting the zero signal. It should be noted that since the LMA-3 is non-linear in this measurement region, these data must first be corrected to obtain the actual ambient mixing ratios. The model curve shown in FIG. 2 could be used to correct for non-linearity. A further 1.04% correction must be applied to these data since the calibration was carried out with the ozone scrubber removed. The "$NO_2$" mode is named for historical reasons. It is the unscrubbed mode, so it actually represents the sum of ozone and $NO_2$. The Figure shows the signal from a second LMA-3 that was used unmodified for reference purposes. These signals must also be corrected for non-linearities and zeros. Finally, the last signal represents $Nox = NO + NO_2$, which was derived by passing the ambient air through a $CrO_3$ converter.

SUMMARY OF DISCLOSURE

In summary of this disclosure, the present invention provides a novel method of determining the concentration of nitrogen dioxide in a gas stream also containing ozone. Modifications are possible within the scope of this invention.

What we claim is:

1. In a method of determining the concentration of nitrogen dioxide in a gas sample containing nitrogen dioxide and ozone, the improvement which comprises selectively removing said ozone from said gas sample prior to said determination by contacting said gas sample with a reducing agent having a redox potential below that of ozone and above or near that of nitrogen dioxide, said reducing agent being a multivalent metal compound selected from the group consisting of the lower valent form of antimony, arsenic, thallium, vanadium, manganese and copper oxides, sulfates, chlorides and nitrates.

2. The method of claim 1 wherein said reducing agent is antimony oxide.

3. The method of claim 1 wherein said gas sample comprises an air stream and said air stream is passed in contact with said reducing agent by flowing the air stream through a chamber in which said reducing agent is located in particulate form supported to contact said air stream.

4. A method of determining the concentrations of nitrogen dioxide and ozone in a gas sample by luminol chemiluminescence, which comprises:
    making a first determination of the nitrogen dioxide concentration in said gas sample by luminol chemiluminescence,
    passing said gas sample into contact with a selective reducing agent for ozone in preference to nitrogen dioxide, said reducing agent being a multivalent metal compound selected from the group consisting of the lower valent form of antimony, aresenic, thallium, vanadium, manganese and copper oxides, sulfates, chlorides and nitrates,
    making a second determination of the nitrogen dioxide concentration of said gas sample by luminol chemiluminescence following said contact of said gas sample with said selective reducing agent, as the true determination of the nitrogen dioxide concentration in said gas sample, and
    subtracting the second determination from the first determination to provide a third determination corresponding to the ozone concentration in said gas sample.

5. The method of claim 4 wherein said selective reducing agent is antimony trioxide.

* * * * *